US011987836B2

(12) United States Patent
Heller et al.

(10) Patent No.: US 11,987,836 B2
(45) Date of Patent: May 21, 2024

(54) METHOD FOR NUCLEIC ACID ANALYSIS DIRECTLY FROM AN UNPURIFIED BIOLOGICAL SAMPLE

(71) Applicant: Global Life Sciences Solutions USA LLC, Marlborough, MA (US)

(72) Inventors: Ryan Charles Heller, Niskayuna, NY (US); Nichole Lea Wood, Niskayuna, NY (US); Robert Scott Duthie, Niskayuna, NY (US); John Richard Nelson, Niskayuna, NY (US); Wei Gao, Niskayuna, NY (US); Michael James Rishel, Niskayuna, NY (US); Klaus Gustav Hentrich, Cardiff (GB)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 178 days.

(21) Appl. No.: 15/510,331

(22) PCT Filed: Sep. 17, 2015

(86) PCT No.: PCT/US2015/050760
§ 371 (c)(1),
(2) Date: Mar. 10, 2017

(87) PCT Pub. No.: WO2016/053638
PCT Pub. Date: Apr. 7, 2016

(65) Prior Publication Data
US 2017/0298415 A1 Oct. 19, 2017

Related U.S. Application Data

(60) Provisional application No. 62/057,401, filed on Sep. 30, 2014.

(51) Int. Cl.
*C12Q 1/6806* (2018.01)
*C12Q 1/6844* (2018.01)
*C12Q 1/6858* (2018.01)
*C12Q 1/6869* (2018.01)

(52) U.S. Cl.
CPC ......... *C12Q 1/6806* (2013.01); *C12Q 1/6844* (2013.01); *C12Q 1/6858* (2013.01); *C12Q 1/6869* (2013.01)

(58) Field of Classification Search
CPC .............. C12Q 1/6806; C12Q 1/6844; C12Q 2521/501; C12Q 2531/125; C12Q 1/6869
See application file for complete search history.

(56) References Cited

U.S. PATENT DOCUMENTS 5,705,345 A  1/1998  Lundin et al.
5,756,126 A *  5/1998  Burgoyne ........... C12N 15/1006
                                                                                422/504
7,053,207 B2 *  5/2006  Wengel ..................... C07H 9/04
                                                                                435/325
2002/0068708 A1 *  6/2002  Wengel ................... C07H 21/00
                                                                                514/44 A
2003/0077609 A1 *  4/2003  Jakobsen ............... C07H 21/00
                                                                                435/6.11
2004/0219565 A1 * 11/2004  Kauppinen ............ C07H 19/06
                                                                                435/5
2007/0269803 A1 * 11/2007  Arar ..................... C12Q 1/6876
                                                                                435/6.11
2008/0131876 A1  6/2008  Hantash
2009/0263871 A1  10/2009  Walker et al.
2010/0062947 A1  3/2010  De Laat et al.
2012/0164651 A1  6/2012  Kazakov et al.
2013/0210078 A1  8/2013  Nelson et al.
2014/0038238 A1  2/2014  Zhang
2014/0113294 A1  4/2014  Horton et al.
(Continued)

FOREIGN PATENT DOCUMENTS

WO   WO-2008099196 A1 *  8/2008  ........... B01L 3/5023
WO     2010/066908 A1    6/2010
(Continued)

OTHER PUBLICATIONS

Mashimo et al., "Detection of small RNA molecules by a combination of branched rolling circle amplification and bioluminescent pyrophosphate assay," Anal. Bioanal. Chem., vol. 401, pp. 221-227. (Year: 2011).*
Ballantyne et al., "Locked nucleic acids in PCR primers increase sensitivity and performance," Genomics, vol. 91, pp. 301-305. (Year: 2008).*
Kore et al., "Synthesis and application of MeOSuc—Ala—Al-Pro-Phe—CH2Cl as potent proteinase K inhibitor," Bioorganic & Medicinal Chemistry Letters, vol. 19, pp. 1296-1300. (Year: 2009).*
Rajendram et al., "Long-term storage and safe retrieval of DNA from microorganisms for molecular analysis using FTA matrix cards," Journal of Microbiological Methods, vol. 67, pp. 582-592. (Year: 2006).*

(Continued)

*Primary Examiner* — Young J Kim
(74) *Attorney, Agent, or Firm* — Eversheds Sutherland (US) LLP

(57) ABSTRACT

A method is provided for generating single-stranded DNA circles from a biological sample. The method comprises the steps of: treating the biological sample with an extractant to release nucleic acids, thereby forming a sample mixture; neutralizing the extractant; denaturing the released nucleic acids to generate single-stranded nucleic acids; and contacting the single-stranded nucleic acids with a ligase that is capable of template-independent, intramolecular ligation of single-stranded DNA to generate the single-stranded DNA circles. All the steps of the method are performed without any intermediate nucleic acid isolation or nucleic acid purification. The single-stranded DNA circles may be amplified and further analyzed. Also provided is a kit which comprises compositions for carrying out the novel methods.

7 Claims, 5 Drawing Sheets

Figure 1:
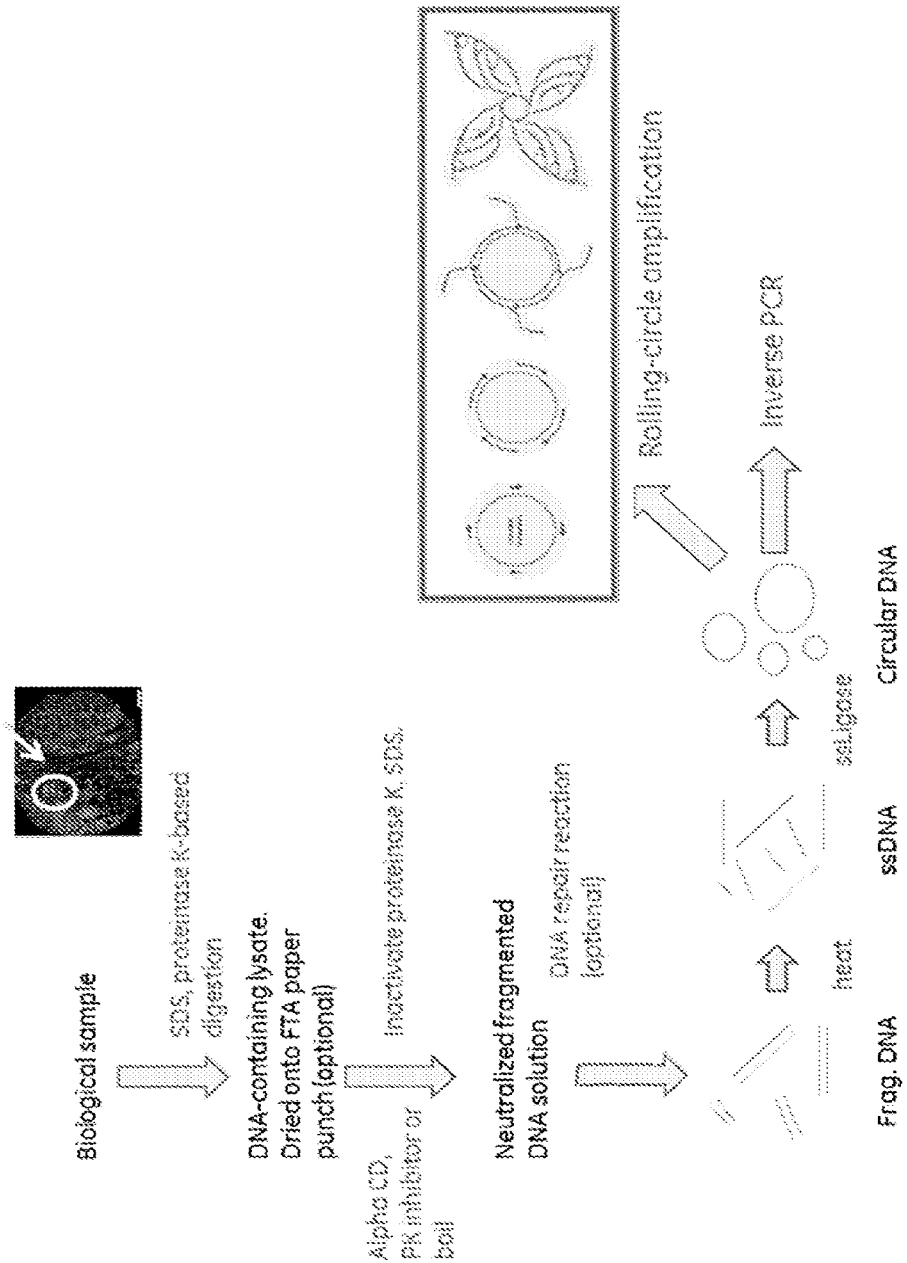

Specification includes a Sequence Listing.

(56) References Cited

U.S. PATENT DOCUMENTS

2016/0053307 A1* 2/2016 Heller .............. C12Q 1/6844
   506/2
2016/0304954 A1* 10/2016 Lin .................. C12Q 1/6827

FOREIGN PATENT DOCUMENTS

WO 2010/094040 A1 8/2010
WO 2014/064169 A1 5/2014

OTHER PUBLICATIONS

Hamburger et al., "Evaluation of Loop-Mediated Isothermal Amplification Suitable for Molecular Monitoring of Schistosome-Infected Snails in Field Laboratories," Am. J. Trop. Med. Hyg., vol. 88, No. 2, pp. 344-351. (Year: 2013).*

Senguven et al., "Comparison of Methods for the Extraction of DNA from Formalin-Fixed, Paraffin-Embedded Archival Tissues," Int. J. Med. Sci., Mar. 27, vol. 11, pp. 494-499. (Year: 2014).*

O'Kane et al., "Direct polymerase chain reaction amplification of formalin-fixed, paraffin-wax-embedded tissue after automated sequential laser microdissection and pressure catapulting," J. Clin. Pathol., vol. 60, pp. 216-217. (Year: 2007).*

Good, N.E., and Izawa, S., "Hydrogen ion buffers," Methods in Enzymology, vol. 24, pp. 53-68 (1972) (Abstract).

Good, N.E., et al., "Hydrogen Ion Buffers for Biological Research," Biochemistry, Issue 5, No. 2, pp. 467-477 (1966) (Abstract).

Hosono, S., et al., "Unbiased Whole-Genome Amplification Directly From Clinical Samples," Genome Research, vol. 13, No. 5, pp. 954-964 (May 1, 2003).

Koshkin, A.A., et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedro, vol. 54, Issue 14, pp. 3607-3630 (Apr. 2, 1998) (Abstract).

Nunez, A.N., et al., "Application of Circular Ligase to Provide Template for Rolling Circle Amplification of Low Amounts of Fragmented DNA," pp. 1-7 (2008).

Singh, S.K., et al., "LNA (locked nucleic acids): Synthesis and High-Affinity Nucleic Acid Recognition," Chemical Communications, vol. 29, No. 4, pp. 455-456 (Feb. 1998) (Abstract).

Tate, C.M., et al., "Evaluation of circular DNA substrates for whole genome amplification prior to forensic analysis," Forensic Science International, vol. 6, Issue 2, pp. 185-190 (May 12, 2011) (Abstract).

Extended European Search Report and Opinion issued in connection with corresponding EP Application No. 15846311.7 dated Mar. 20, 2018.

International Search Report and Written Opinion regarding International Application No. PCT/US2015/050760, dated Dec. 18, 2015, 10 pages.

* cited by examiner

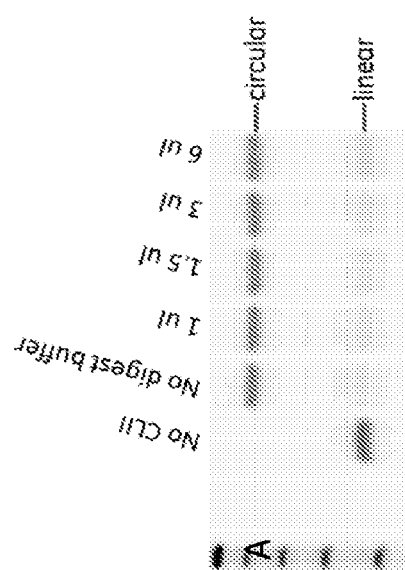
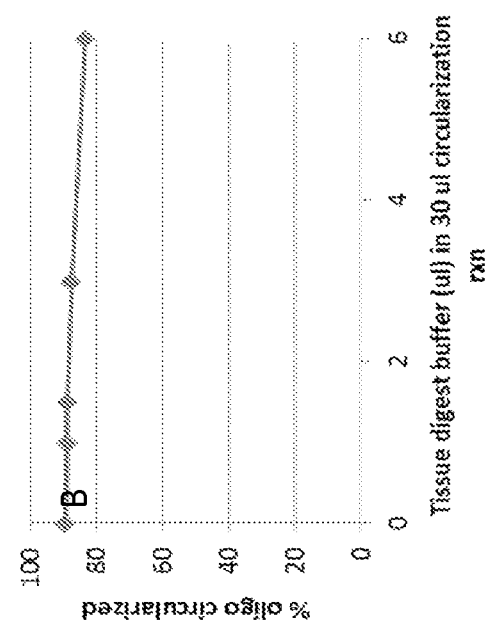
FIG. 2A
FIG. 2B

METHOD FOR NUCLEIC ACID ANALYSIS DIRECTLY FROM AN UNPURIFIED BIOLOGICAL SAMPLE

CROSS-REFERENCE TO RELATED APPLICATIONS

This application is a filing under 35 U.S.C. 371 of international application number PCT/US2015/050760, filed Sep. 17, 2015, which claims priority to U.S. application No. 62/057,401, filed Sep. 30, 2014, the entire disclosures of each of which are hereby incorporated by reference.

SEQUENCE LISTING

The instant application contains a Sequence Listing which has been filed electronically in ASCII format and is hereby incorporated by reference in its entirety. Said ASCII copy, created on May 17, 2019, is named 34428-0362_SL.txt and is 622 bytes in size.

FIELD OF INVENTION

The invention generally relates to nucleic acid analysis. More specifically, the invention relates to a method for the circularization of nucleic acid molecules via template-independent single-stranded DNA ligation, from a biological sample. It further relates to the amplification and/or detection of the single-stranded DNA circles. Generation of single-stranded DNA circles is performed in a single reaction vessel directly from a biological sample, without any intervening isolation and/or purification steps. Kits for performing the methods are also provided.

BACKGROUND

The analysis of nucleic acids is widely used in clinical and applied fields, as well as in academic research. While abundant supply of quality biological sample is available for some samples/fields, in many instances the sample may be rare or damaged. For example, in cancer research and diagnostics, it is increasingly desirable to analyze nucleic acids from formalin-fixed, paraffin embedded (FFPE) tissue samples, as well as from specific regions of interest within a sample. In some cases, the analysis of only a few cells is desirable. Currently many fixed tissue samples following DNA extraction do not provide sufficient DNA for analyses such as targeted resequencing and PCR-based diagnostic tests and often the DNA is of poor quality, further limiting the effectiveness of these tests.

Whole-genome amplification (WGA) involves non-specific amplification of a target DNA. WGA is often achieved by multiple displacement amplification (MDA) techniques employing random oligonucleotide primers for priming the DNA synthesis at multiple locations of the target DNA along with a high fidelity DNA polymerase having strand displacing activity (e.g., Phi29 polymerase) in an isothermal reaction. Even though currently available commercial WGA MDA systems such as GenomiPhi (GE Healthcare, USA) and RepliG (Qiagen) kits provide optimal results with high molecular weight target DNA, performance of these systems is poor when the target DNA is short and/or highly fragmented. When the target sequence length is less than about 1,000 nucleotides, amplification of the target DNA using conventional methods results in decreased amplification speed, significant sequence dropout particularly near the ends of the target DNA, and highly sequence-biased amplification. Some of this is related to the observation that as the length of the template DNA is decreased, the likelihood of the template being primed multiple times decreases in the MDA reaction. This decreases the amplification potential of these shorter fragments. Efficient methods for non-specifically amplifying short, fragmented DNA are therefore highly desirable.

Ligation-mediated polymerase chain reaction (PCR) has been used to amplify fragmented dsDNA. However, only a small fraction of the fragmented DNA is amplified in these reactions leading to inadequate genome coverage. To efficiently amplify fragmented dsDNA, the template may first be enzymatically repaired and then be concatemerized by blunt-end ligation to generate sequences that are longer than 1000 base pairs (bp). However, a relatively high concentration of the target DNA is often required to promote intermolecular concatemerization and subsequent amplification. Circularization of double-stranded target DNA has also been employed in various nucleic acid based assays including MDA, WGA, hyper-branched rolling circle amplification (RCA) and massively parallel DNA sequencing. To effectively circularize and amplify fragmented dsDNA, the double-stranded ends of the fragmented DNA are first repaired, followed by blunt-end ligation to form double-stranded DNA circles. However, it is difficult to circularize double-stranded DNA fragments that are less than 250 bp in length, and impossible with DNA less than approximately 150 bp in length, as that is the persistence length of double stranded DNA.

The double-stranded DNA may be first denatured to produce single-stranded DNA (ssDNA), and may further be circularized in a template-dependent intramolecular ligation reaction using a scaffold/bridging oligonucleotide and a ligase. However, prior sequence information of the target DNA is required to perform a template-dependent circularization. Template-independent intramolecular ligation of ssDNA has also been documented. For example, TS2126 RNA ligase (commercially available under the trademarks ThermoPhage™ RNA ligase II or ThermoPhage™ ssDNA ligase (Prokaria, Matis, Iceland) or CircLigase™ ssDNA ligase (Epicentre Biotechnologies, Wisconsin, USA) has been used for making digital DNA balls, and/or locus-specific cleavage and amplification of DNA, such as genomic DNA. From limited amounts of fragmented DNA, DNA template for rolling circle amplification has also been generated by employing TS2126 RNA ligase. The method involved denaturing the linear, fragmented dsDNA to obtain linear ssDNA fragments, ligating the linear ssDNA with CircLigase™ ssDNA ligase to obtain single-stranded DNA circle, and then amplifying the single-stranded DNA circle using random primers and Phi29 DNA polymerase via RCA.

Moreover, all attempts of ligation-amplification reactions involved intermediate isolation, purification and/or cleaning steps, thus making the ligation-amplification workflow cumbersome. For example, analysis of forensic samples of fragmented DNA by circularization followed by rolling circle amplification was carried out in multiple steps comprising 5' DNA phosphorylation, adapter ligation, DNA circularization, and whole-genome amplification. Each step was subjected to a reaction clean-up before performing the next step. No amplification advantage was observed when ligation and amplification was performed in single reaction vessel. However, the multi-step process often resulted in the loss of template DNA and led to failed analysis.

WO2010094040A1 (Epicentre) describes the discovery and use of pre-adenylated phage TS2126 RNA ligase to address variable intramolecular ligation efficiency of linear single-stranded DNA molecules of different sequences and sizes. This enzyme is sold commercially under the name CircLigase II. Only pre-purified DNA was used as the starting material for the intramolecular ligation.

In Forensic Sci Int Genet. 2012 Mar.;6(2):185-90, Tate et al. evaluated a multi-step process for the preparation and treatment of pre-purified genomic DNA samples prior to single-stranded DNA circularization and rolling-circle amplification for the purpose of improving forensic STR profile analysis of limiting quantities of fragmented DNA. They found that STR amplification efficiency was not improved and STR genotyping failed following their multi-step process "presumably due to loss of DNA template as a result of multiple intermediate silica column purification steps, each of which resulted in a loss of template DNA."

Efficient methods for amplifying short DNA sequences in a single reaction vessel without any sequence bias and any intervening cleaning steps, directly from a biological sample, are therefore highly desirable.

BRIEF DESCRIPTION

In one aspect of the invention, a method is provided for generating single-stranded DNA circles from a biological sample. The method comprises the steps of: treating the biological sample with an extractant to release nucleic acids, thereby forming a sample mixture; neutralizing the extractant; denaturing the released nucleic acids to generate single-stranded nucleic acids; and contacting the single-stranded nucleic acids with a ligase that is capable of template-independent, intramolecular ligation of a single-stranded DNA sequence to generate single-stranded DNA circles. All the steps of the method are performed without any intermediate nucleic acid isolation or nucleic acid purification.

In certain embodiments, the steps are performed in a sequential manner in a single reaction vessel.

In certain embodiments, the single-stranded DNA circles are amplified to enable subsequent analysis of the biological sample.

In certain embodiments, the sample mixture is dried on solid matrix prior to the neutralizing step.

In certain embodiments, damage to the DNA is repaired enzymatically prior to the denaturing step.

In a second aspect of the invention, a method is provided for analyzing a biological sample. Thus, the single-stranded DNA circles generated according to certain embodiments of the invention are amplified, and the amplification product is analyzed. The analysis may be performed by, for example, targeted sequencing of the amplified product.

In another aspect of the invention, a method is provided for detecting chromosomal rearrangement breakpoints from a biological sample. Thus, the single-stranded DNA circles generated according to certain embodiments of the invention are amplified, and the amplification product is analyzed, e.g., by sequencing. Any chromosomal rearrangement breakpoints are identified by comparing the sequences to a known reference sequence.

In yet another aspect of the invention, a kit is provided that comprises an extractant for treating a biological sample to release nucleic acids; a reagent for neutralizing the extractant; and a ligase that is capable of template-independent, intramolecular ligation of a single-stranded DNA sequence.

DRAWINGS

These and other features, aspects and advantages of the invention will become better understood when the following detailed description is read with reference to the accompanying figures.

FIG. 1 illustrates a graphical outline of a method workflow according to an embodiment of the invention.

FIG. 2A and FIG. 2B present results of circularization reactions in the presence of varied amount of neutralized extractant.

FIGS. 3A and FIG. 3B present data showing that amplification reaction using high Tm primers are more resistant to carryover inhibition.

Figures 4A, 4B:
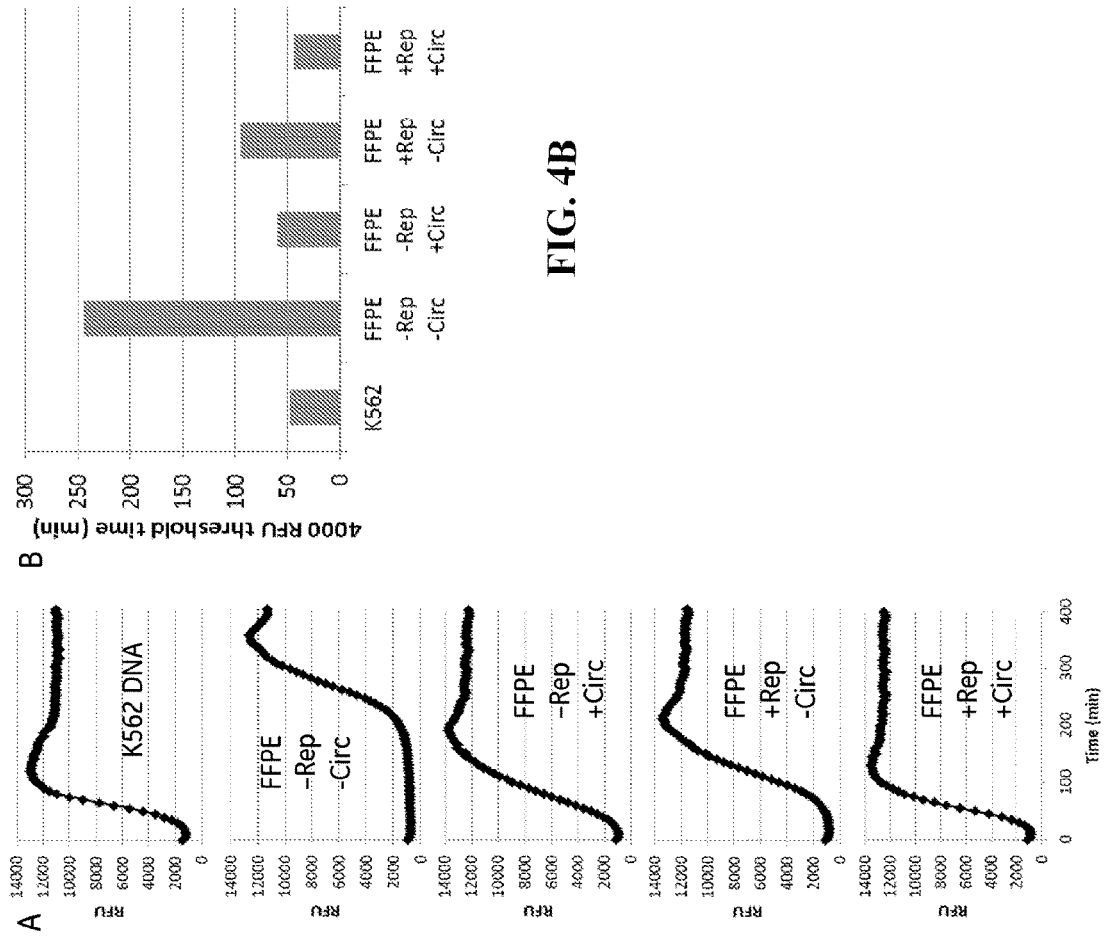

FIGS. 4A and FIG. 4B present data which shows an example of direct amplification of fragmented DNA from human tissue, according to an embodiment of the invention.

Figure 5A:
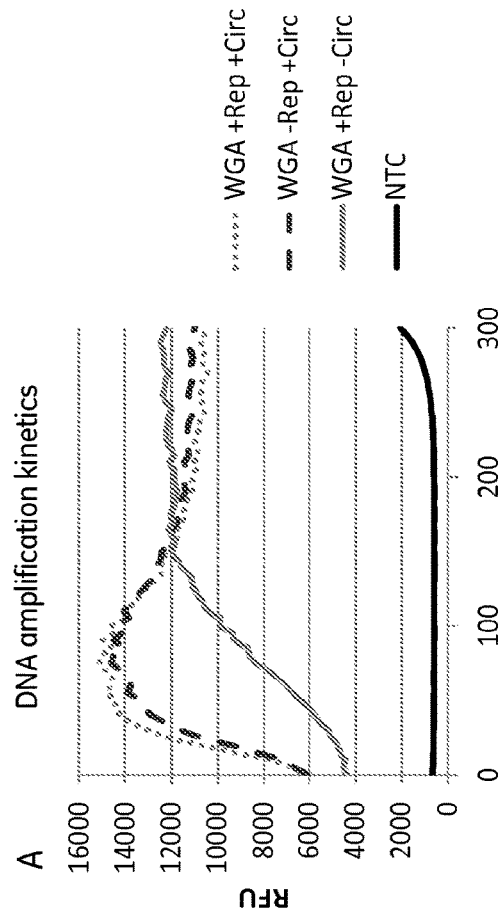
Figure 5B:
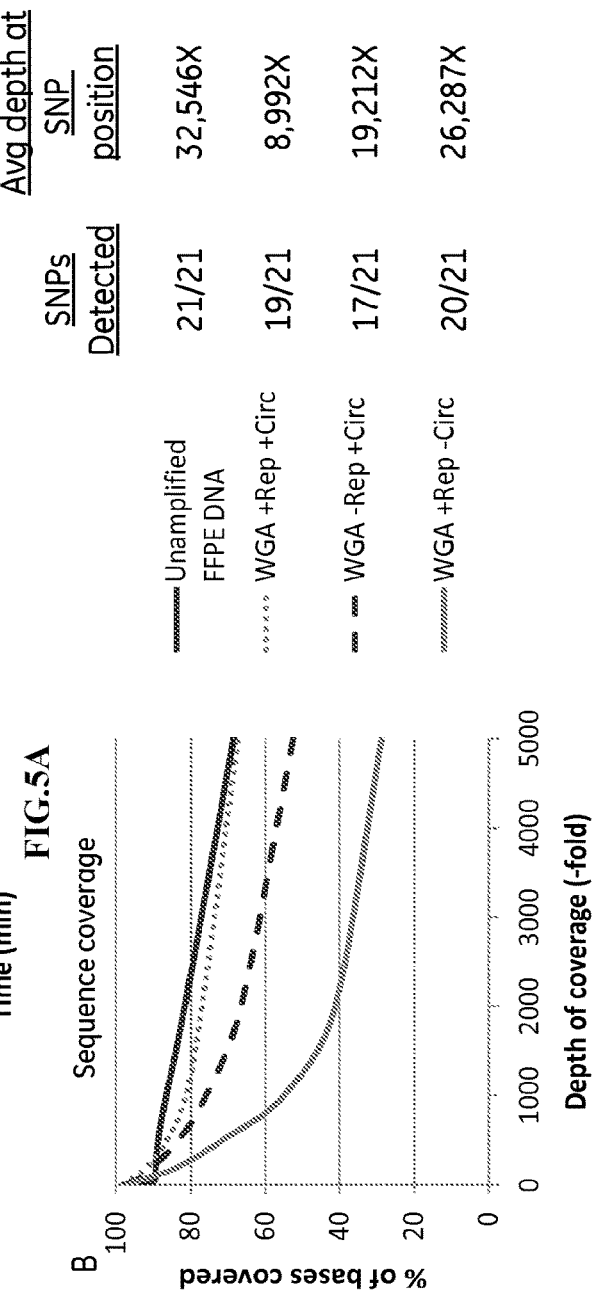

FIG. 5A and FIG. 5B present data demonstrating improved sequence coverage and SNP detection after DNA repair and circularization of a formalin fixed sample, according to an embodiment of the invention.

DETAILED DESCRIPTION

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between. To more clearly and concisely describe and point out the subject matter of the claimed invention, the following definitions are provided for specific terms, which are used in the following description and the appended claims.

As used herein, the term "nucleoside" refers to a glycosylamine compound wherein a nucleic acid base (nucleobase) is linked to a sugar moiety. A "nucleotide" refers to a nucleoside phosphate. A nucleotide may be represented using alphabetical letters (letter designation) corresponding to its nucleoside as described in Table 1. For example, A denotes adenosine (a nucleoside containing the nucleobase, adenine), C denotes cytidine, G denotes guanosine, U denotes uridine, and T denotes thymidine (5-methyl uridine). W denotes either A or T/U, and S denotes either G or C. N represents a random nucleoside and dNTP refers to deoxyribonucleoside triphosphate. N may be any of A, C, G, or T/U.

TABLE 1

Letter designations of various nucleotides.

| Symbol Letter | Nucleotide represented by the symbol Letter |
|---|---|
| G | G |
| A | A |
| T | T |
| C | C |
| U | U |
| R | G or A |
| Y | T/U or C |
| M | A or C |
| K | G or T/U |
| S | G or C |
| W | A or T/U |
| H | A or C or T/U |
| B | G or T/U or C |
| V | G or C or A |
| D | G or A or T/U |
| N | G or A or T/U or C |

As used herein, the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a natural nucleotide, a synthetic nucleotide, a modified nucleotide, or a surrogate replacement moiety (e.g., inosine). Generally, nucleotide analogues with altered nucleobases confer, among other things, different base pairing and base stacking proprieties.

As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998). The 2' and 4' position of the furanose unit in the LNA nucleotide may be linked by an O-methylene (e.g., oxy-LNA: 2'-O, 4'-C-methylene-β-D-ribofuranosyl nucleotide), an S-methylene (thio-LNA), or a NH-methylene moiety (amino-LNA), and the like. Such linkages restrict the conformational freedom of the furanose ring. LNA oligonucleotides display enhanced hybridization affinity toward complementary single-stranded RNA and complementary single- or double-stranded DNA. The LNA oligonucleotides may induce A-type (RNA-like) duplex conformations. Nucleotide analogues having altered phosphate-sugar backbone (e.g., PNA, LNA) often modify, among other things, the chain properties such as secondary structure formation. A star (*) sign preceding a letter designation denotes that the nucleotide designated by the letter is a phosphorothioate modified nucleotide. For example, *N represents a phosphorothioate modified random nucleotide. A plus (+) sign preceding a letter designation denotes that the nucleotide designated by the letter is a LNA nucleotide. For example, +A represents an adenosine LNA nucleotide, and +N represents a locked random nucleotide (i.e., a random LNA nucleotide).

As used herein, the term "BNA (Bridged Nucleic Acid) nucleotide" (2',4'-BNANC (2'-O,4'-aminoethylene bridged nucleic acid), is a compound containing a six-member bridged structure with an N—O linkage. This novel nucleic acid analogue can be synthesized and incorporated into oligonucleotides. When compared to the earlier generation of LNA, BNA was found to possess: higher binding affinity against an RNA complement, excellent single-mismatch discriminating power, enhanced RNA selective binding, stronger and more sequence selective triplex-forming characters, stronger nuclease resistance to endo and exo-nucleases, i.e., even higher than the S(p)-phosphorothioate analogue.

As used herein, the term "oligonucleotide" refers to oligomers of nucleotides. The term "nucleic acid" as used herein refers to polymers of nucleotides. The term "sequence" as used herein refers to a nucleotide sequence of an oligonucleotide or a nucleic acid. Throughout the specification, whenever an oligonucleotide or nucleic acid is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide. The oligonucleotides or nucleic acids may be a DNA, an RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long.

As used herein, the term "random primer" refers to a mixture of primer sequences, generated by randomizing a nucleotide at any given location in an oligonucleotide sequence in such a way that the given location may consist of any of the possible nucleotides or their analogues (complete randomization). Thus the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for whole-genome amplification reactions.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reactions are initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template repeatedly (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a cascade of multiple-hybridization, primer-extension, and strand-displacement events involving both the primers. This often generates a discrete set of concatemeric, double-stranded nucleic acid amplification products. The rolling circle amplification may be performed in vitro under isothermal conditions using a suitable nucleic acid polymerase such as Phi29 DNA polymerase.

As used herein, the term "inverse PCR" refers to a variant of the polymerase chain reaction that is used to amplify DNA with only one known sequence. One limitation of conventional PCR is that it requires primers complementary to both termini of the target DNA, whereas inverse PCR allows PCR to be carried out even if only one sequence is available from which primers may be designed, although it requires a circularized DNA template or for linear template to have direct repeats of the priming sequence. Thus, for a circularized DNA template, primer pairs that are normally binding in the wrong orientation from one another (amplifying outward from a common loci on a linear DNA, which provides only linear amplification kinetics) are instead converging as is required by the PCR for exponential amplification kinetics, to produce an amplification product across the circularization point.

As used herein, the term "solid matrix" refers to a selective barrier that allows the passage of certain constituents and retains other constituents found in the liquid (i.e. membrane), commonly composed of cellulose, glass or quartz fiber/microfiber material, The solid matrix may also be comprised of a porous polymer, for example porous membrane material such as polyester, polyether sulfone (PES), polyamide (Nylon), polypropylene, polytetrafluoroethylene (PTFE), polycarbonate, cellulose nitrate, cellulose acetate, alginate or aluminium oxide. A solid matrix typically has a high surface to volume ratio. The matrix can be either ordered or disordered. Some examples include glass fiber, nitrocellulose, quartz fiber, 903 cards, FTA paper and FTA-elute paper.

In some embodiments, the invention provides a method for the DNA extraction, optional enzymatic repair, and single-stranded DNA circularization of fragmented DNA from a biological source. Thus, one embodiment of the invention provides a method for generating single-stranded DNA circles from a biological sample, the method comprising:
  (A) treating the biological sample with an extractant to release nucleic acids, thereby forming a sample mixture;
  (B) neutralizing the extractant;
  (C) denaturing the released nucleic acids to generate single-stranded nucleic acids; and
  (D) contacting the single-stranded nucleic acids with a ligase that is capable of template-independent, intramolecular ligation of a single-stranded DNA sequence to generate the single-stranded DNA circles,
wherein all the steps of the method are performed without any intermediate nucleic acid isolation or nucleic acid purification. In certain embodiments, steps (A) to (D) are performed in a sequential manner in a single reaction vessel (e.g., eppendorf tube). Steps (B) and (C) can be performed in either order.

The biological sample (e.g., a sample obtained from a biological source) may be formalin-fixed tissue, fixed individual cells, blood plasma, ancient tissue samples, or other environmentally exposed biological samples. For example, the biological sample may be obtained from, but not limited to, bodily fluid (e.g., blood, blood plasma, serum, urine, milk, cerebrospinal fluid, pleural fluid, lymph, tear, sputum, saliva, stool, lung aspirate, throat or genital swabs), organs, tissues, cell cultures, cell fractions, sections (e.g., sectional portions of an organ or tissue) or cells isolated from the biological subject or from a particular region (e.g., a region containing diseased cells) of the sample from a biological subject. The biological sample may be of eukaryotic origin, prokaryotic origin, viral origin or bacteriophage origin.

The biological sample is treated with an extractant to release nucleic acids, thereby forming a sample mixture. An extractant is added to the sample in order to lyse the tissue/cells, and/or solubilize/digest proteins, providing accessible nucleic acids for downstream reactions. The extractant is then neutralized to inactivate the extractant which would otherwise inhibit downstream enzymatic reactions. In certain embodiments, the extractant is neutralized by adding a sequestrant. In other embodiments, the extractant is neutralized by a physical condition change, such as heating. The term "extractant" refers to a composition that breaks up the tissue or cells, and solubilizes/digests proteins, to render the nucleic acids amendable for the downstream reactions. The term "sequestrant" refers to a composition that neutralizes the effect of the extractant. For example, if the extractant includes a base, then an acid may be used to bring the solution to neutral. For example, proteinase K may be used as the extractant when the biological sample is blood plasma, and a proteinase K inhibitor is used as the sequestrant to neutralize the proteinase K. Alternatively, a heating step may be used to inactivate proteinase K. In certain embodiments, the extractant includes a detergent, such as SDS. A sequestrant comprising a cyclodextrin may be used to neutralize the effect of SDS.

The nucleic acid from the biological sample may be genomic DNA, mitochondrial DNA, microbial DNA, viral DNA or other DNA source. The DNA may be fragmented. The length of the nucleic acid from the biological sample may range from 15 nucleotides to 21,000 nucleotides. Due to persistence length, it is not generally possible to circularize dsDNA that has a sequence length smaller than 150 bp, and it is very difficult to circularize dsDNA until the DNA is longer than 200 bp. In contrast, linear ssDNA molecules having a sequence length of 15 nucleotides (nt) or more are very efficiently circularized by a suitable ligase provided the 5' end is phosphorylated and the 3' end is hydroxylated. For nucleic acids in plasma, they are generally about 150-180 bp long and thus circularize with low yield as double-stranded DNA. In old FFPE sample (>20 years old), DNA is very fragments are mostly 60-70 nt long. The methods according to certain embodiments of the invention are uniquely suited for analysis of such biological samples.

The nucleic acid from the neutralized sample is denatured to a single-stranded form prior to the intramolecular ligation reaction. This may be achieved by using any of the art-recognized methods for the conversion of dsDNA to ssDNA sequences. For example, the dsDNA may be thermally denatured, chemically denatured, or both thermally and chemically denatured. The dsDNA may be chemically denatured using a denaturant (e.g., base, glycerol, ethylene glycol, formamide, urea or a combination thereof) that reduces the melting temperature of dsDNA. The denaturant may reduce the melting temperature by 5° C. to 6° C. for every 10% (vol./vol.) of the denaturant added to the reaction mixture. The denaturant or combination of denaturants (e.g., 10% glycerol and 6-7% ethylene glycol) may comprise 1%, 5%, 10%, 15%, 20%, or 25% of reaction mixture (vol./vol.). Salts that reduce hybridization stringency may be included in the reaction buffers at low concentrations to chemically denature the dsDNA at low temperatures. The dsDNA may be thermally denatured by heating the dsDNA, for example, at 95° C.

After the denaturing step, the generated ssDNA may be treated with a DNA or RNA ligase that is capable of intra-molecular ligation of ssDNA substrates in the absence of a template to form the single-stranded DNA circles. Suitable ligases that may be used for the ligation reaction include, but are not limited to, TS2126 RNA ligase, T4 DNA ligase, T3 DNA ligase or *E. coli* DNA ligase.

In some embodiments, conversion of the ssDNA to single-stranded DNA circle is performed with a thermally stable RNA ligase that has efficient template-independent, intramolecular ligation activity for linear ssDNA substrates that have 5' phosphoryl and 3' hydroxyl groups. The ligase may be in a substantially pre-adenylated form. For example, TS2126 RNA ligase derived from the Thermus bacteriophage TS2126 that infects the thermophilic bacterium, *Thermus scotoductus* may be employed for template-independent circularization of the fragmented linear ssDNA to circular ssDNA. TS2126 RNA ligase is more thermally stable (stable up to about 75° C.) than many of the mesophilic RNA ligases such as the T4 RNA ligases. The range of temperature for TS2126 RNA ligase activity can be greater than about 40° C., for example, from about 50° C. to about 75° C. Due to this, TS2126 RNA ligase may be used at higher temperatures, which further reduce undesirable secondary structures of ssDNA. The circularization of linear ssDNA may also be achieved by a ligase other than TS2126 RNA ligase or by employing any other enzyme having DNA joining activity such as topoisomerase. In some embodiments, the circularization of fragmented, single-stranded DNA molecule is achieved by an RNA ligase 1 derived from thermophilic archaebacteria, *Methanobacterium thermoautotrophicum* (Mth RNA ligase) that has high template-independent ligase activity in circularizing linear, fragmented ssDNA molecules.

In some embodiments, a method for improving the efficiency of circularization of ssDNA by TS2126 RNA ligase is provided. Use of HEPES buffer having a pH of 8.0 for the ligation reaction increased the ligation efficiency. Template-independent ssDNA ligation was inefficient when the reaction was performed in TRIS buffer (e.g., For CircLigase™ II, the suggested 10× reaction buffer by EpiCentre comprises 0.33 M TRIS-Acetate (pH 7.5), 0.66 M potassium acetate, and 5 mM DTT). Further, manganese, an essential co-factor for the ligation reaction, is rapidly oxidized under alkaline conditions and forms a precipitate in the presence of TRIS. Air oxidation of $Mn^{2+}$ to $Mn^{3+}$ may be facilitated by the anions that can strongly complex the $Mn^{3+}$ ions. For example, when equal volumes of 0.2 mol/liter Tris with pH appropriately adjusted with HCl and 2 mmol/liter $MnCl_2$ were mixed, the color change was immediate at pH 9.3 (the pH of TRIS base alone); had an initial time lag of about 3 minutes at pH 8.5. Although the reaction did not occur at lower pH, the changes observed at higher pH were not reversed by adding acid. Due to rapid oxidation of manganese in TRIS buffer, a higher concentration of manganese is essential for the ligation reaction (e.g., addition of $MnCl_2$ to a final concentration of 2.5 mM) when the intramolecular ligation is performed in TRIS buffer. Further, it becomes difficult to accurately predict the working concentration of manganese in the reaction as the manganese concentration continues to decrease over time. Higher concentrations of manganese may lead to higher error-rate of the polymerase during amplification when the ligation and amplification is performed in a single reaction vessel. By substituting TRIS buffer with HEPES buffer in the ligation reaction, effective intra-molecular ligation may be achieved with manganese ion concentration less than 0.5 mM. Apart from HEPES, any of other the Good's buffers (see, for example, Good, Norman et al. Biochemistry, 5 (2): 467-477, 1966; and Good, Norman et al., Methods Enzymol., 24: 53-68, 1972.) may be employed for the intramolecular ligation reaction.

In certain embodiments, after the biological sample is treated with an extractant to release nucleic acids, and before the neutralizing step, the sample mixture is optionally subjected to a drying step on a solid matrix. The application of the sample to a solid matrix may reduce shearing of the resulting nucleic acid by preventing shear forces associated with sample handling, mixing and pipetting. This may result in more intact nucleic acid. The more intact nucleic acid may be repaired more effectively. For instance, if the double stranded DNA is substantially nicked and the gentle handling prevents the DNA from being dissociated between nick sites, the DNA ligation step is therefore more effective. The drying step may increase cellular lysis and protein denaturation efficiency, thereby releasing a larger quantity and more accessible nucleic acid. Furthermore, gentle lysis and immobilized DNA can promote more efficient repair reaction. Additionally, drying also allows the sample to be stored temporarily in a stable format, allowing greater flexibility with regard to workflow timing.

In certain embodiments, the solid matrix is glass fiber filters or quartz fiber filters (QMA). In certain other embodiments, the solid matrix is a cellulose fiber paper such as a FTA paper, FTA Elute paper, or Whatman 903 paper. FTA paper (including FTA microcards, FTA indicating, and FTA classic) is a cellulose fiber paper treated with nucleic acid extracting and stabilizing chemicals, for example a weak base, a chelating agent and an anionic surfactant, whereby the support surface is impregnated with the stabilization chemicals. FTA Elute herein describes similar paper but coated with a chaotropic agent such as guanidinium thiocyanate. Herein Whatman 903 describes uncoated cellulose fiber paper. In certain embodiments the nucleic acid extracting and stabilizing chemicals can be added to the solid matrix after the sample is applied.

In certain embodiments, after the neutralizing step but before the denaturing step, the sample mixture is optionally subjected to a step of repairing DNA damage or removal of DNA lesions. For example, uracil DNA glycosylase (UDG) may be used to excise uracil bases which can occur due to the deamination of cystosine. Formamidopyrimidine [fapy]-DNA glycosylase (fpg) may be used to remove damaged purines. Apurinic apyrimidinic endonuclease (APE1 and Endo IV) may be used to nick DNA at abasic sites and sites of oxidative damage. DNA polymerase I may be used to replace damaged bases at or near nick sites, and T4 DNA ligase may be used to join nicked sites, Further, T4 polynucleotide kinase may be used to generate DNA ends that are compatible for ligation on those fragments that normally would not be competent for circularization (phosphorylate DNA ends that have a 5'-OH and dephosphorylate DNA ends that have a 3'-phosphate group).

A major benefit of the method is the ability to perform each of the sequential manipulations without any intermediate purification steps that would inevitably result in DNA loss. The method allows for the analysis of much smaller amounts of biological material than would be possible if purification steps were required. Thus, the method enables DNA analysis from a small amount of biological sample such as a few cells, or a small region of interest (ROI) or under circumstances where the quantity of extracted DNA is limiting, or of low quality, and where DNA purification steps are not feasible or would result in unsatisfactory DNA loss or require complicated and time-consuming sample manipulation.

For example, by selecting a small region of interest from an FFPE tissue slide this method would enable more reliable detection of DNA sequence alterations and structural changes such as chromosomal rearrangements from specific cells in a target region. This is advantageous as the small sample is more pure, as it is not diluted within a larger tissue sample that may be heterogeneous in cell composition. In addition, this method may be utilized from fixed cells either on a slide or otherwise collected. For example such as from isolated circulating tumor cells or a fine needle aspirate where cells are discrete and in a mixture, and especially where DNA amplification is required for genetic analysis.

The circularization reaction is of particular importance when working with fragmented DNA sources because it allows for subsequent amplification and analysis using reactions such as rolling-circle amplification and inverse PCR. Standard multiple-displacement amplification reactions do not work efficiently on fragmented DNA less than approximately 1000 nt, producing DNA that has high levels of sequence dropout especially near the ends of the molecules and in addition, produces highly biased amplification. Converting the fragmented input DNA into single-stranded circles enables DNA amplification to proceed via a highly sensitive and efficient rolling circle mechanism.

Thus, according to certain embodiments of the invention, the circularized single-stranded DNA circles are further amplified. The amplification may be performed using random primers comprising locked nucleic acid nucleotides or bridged nucleic acid nucleotides or unmodified deoxyribonucleic acid nucleotides.

For example, the ssDNA circles in the ligation reaction mixture may be amplified under isothermal conditions via rolling circle amplification (RCA) methods. The amplification reagents including DNA polymerase, primers and dNTPs may be added to the same reaction vessel to produce an amplification reaction mixture and to initiate an RCA reaction. The amplification reaction mixture may further include reagents such as single-stranded DNA binding proteins and/or suitable amplification reaction buffers. The amplification of ssDNA circles is performed in the same reaction vessel in which ligation is performed. Isolation or purification of the ssDNA circles and/or removal of the ligase is not necessary prior to the amplification reaction. The amplified DNA may be detected by any of the currently known methods for DNA detection or DNA sequencing.

RCA may be performed by using any of the DNA polymerases that are known in the art such as a Phi29 DNA polymerase or Bst DNA polymerase. It may be performed using a random primer mixture or by using a specific primer. In some embodiments, random primers are used for the RCA reaction. Primer sequences comprising one or more nucleotide analogues (e.g., LNA nucleotides, 2-Amino-dA, or 2-Thio-dT modification) may also be used. In some embodiments, nuclease-resistant primers (e.g., primer sequences comprising phosphorothioate groups at appropriate positions) are employed for the amplification reactions (e.g., NNNN*N*N). In some embodiments, RCA may be performed by contacting the ssDNA circles with a primer solution comprising a random primer mixture to form a nucleic acid template-primer complex; contacting the nucleic acid template-primer complex with a DNA polymerase and deoxyribonucleoside triphosphates; and amplifying the nucleic acid template. In some embodiments the primers may have a randomized 3' end, but with a fixed sequence at the 5' end to enable further manipulation of the amplification product later.

Alternatively, the ssDNA circles in the ligation reaction mixture may be amplified by inverse PCR. The amplification reagents including a thermostable DNA polymerase, primers and dNTPs may be added to the same reaction vessel to produce an amplification reaction mixture and to initiate a PCR reaction. The amplification reaction mixture may further include reagents such as single-stranded DNA binding proteins and/or suitable amplification reaction buffers. The amplification of ssDNA circles is performed in the same reaction vessel in which ligation is performed. Isolation or purification of the ssDNA circles and/or removal of the ligase is not necessary prior to the amplification reaction. The amplified DNA may be detected by any of the currently known methods for DNA detection or DNA sequencing.

In certain embodiments, the single-stranded DNA circles may first be amplified via rolling circle amplification, followed by PCR or inverse PCR or a combination of PCR and inverse PCR together.

Certain embodiments of the invention provide methods to detect DNA from biological material that previously was impossible to detect. In the past, before performing single-stranded DNA circularization reactions, it was necessary for DNA to be purified from the other biological components after lysis of the sample. Epicentre (WO2010094040A1)_ provides only an optimized method for converting purified single-stranded DNA fragments with 5'-phosphate and 3'-hydroxyl ends into single-stranded circular molecules. In many situations, however, DNA quantity is limited, the DNA is damaged, and/or the DNA may not have ligatable ends. In these situations, a purification step will result in an unacceptable DNA loss and can result in shearing of the DNA because of the additional manipulation. Further, damaged DNA and DNA with incompatible ends will further reduce the quantity of useful DNA for analysis. For example, attempts to circularize and amplify limited amount of DNA using a method that includes multiple purification steps (Tate et al. Forensic Science International: Genetics Volume 6, Issue 2, Pages 185-190) have failed presumable because of DNA loss. Certain embodiments of the invention provides methods that allow the DNA repair, single-stranded DNA circularization, and amplification reactions to proceed efficiently even with crude lysate. The crude lysate contains a number of biological molecules such as proteins, lipids, carbohydrates, as well as chemicals used for extracting the DNA. These molecules may potentially interfere with enzymatic reactions. Yet single-stranded nucleic acid circles are successfully generated and further amplified using the novel methods.

FIG. 1 is a graphical outline of a workflow according to an embodiment of the invention. As shown, fragmented DNA is extracted directly from unpurified material using a buffer containing SDS and proteinase K. These chemicals are then neutralized, followed by an optional repair of the DNA, denaturation into single strands, and circularization using a single-stranded ligase. These circular molecules are suitable for amplification by RCA or by analysis using inverse PCR and outward-facing primers. The following is a detailed description of each step:

Cell lysis/tissue digestion—A biological sample, such as a FFPE tissue sample, fixed individual cells, blood plasma, ancient tissue sample, environmentally exposed sample, is incubated with a buffered solution containing SDS and proteinase K for >1 hour to break down the tissue, lyse cells, and extract DNA. Optionally, the lysate is dried onto FTA paper, which aids in cell lysis, preserves the DNA, and aids with the subsequent DNA repair reaction.

Inactivation of proteinase K and SDS—Proteinase K and SDS are highly inhibitory to the subsequent optional repair, circularization, and DNA amplification reactions and must be inactivated prior to these steps. The crude lysate/dried punch is incubated with a solution that contains alpha-cyclodextrin to sequester free SDS to render it unable to inhibit/denature enzymes in downstream reactions. One method for inactivating proteinase K is by heating at high temperature, which has the drawback of denaturing DNA, preventing the repair reaction from utilizing complementary sequence to fill gaps and synthesize intact DNA. Another method to inactivate proteinase K is to utilize a proteinase K inhibitor (EMD Millipore, peptide sequence MeOSuc-Ala-Ala-Pro-Phe-CH$_2$Cl (SEQ ID NO: 1)), which irreversibly inactivates the proteinase K at room temperature.

Optional DNA repair or DNA lesion removal—If needed, the crude DNA solution is incubated in a reaction with a cocktail of one or more enzymes: uracil DNA glycosylase (UDG) to excise uracil bases which can occur due to the deamination of cystosine, apurinic apyrimidinic endonuclease (APE1 and Endo IV) to nick DNA at abasic sites and sites of oxidative damage, formamidopyrimidine [fapy]-DNA glycosylase (fpg) to remove damaged purines, DNA polymerase I to excise damaged bases at both the 5' and 3' end of DNA, DNA polymerase I and T4 DNA ligase to repair DNA at or near nicked sites, and T4 polynucleotide kinase to generate DNA ends that are compatible for ligation on those fragments that normally would not be competent for circularization (phosphorylate DNA ends that have a 5'-OH and dephosphorylate DNA ends that have a 3'-phosphate group).

DNA circularization—First, the fragmented input DNA is heated at 95 degrees C. in order to denature the double-stranded DNA into single strands. Next, a buffer containing HEPES, potassium acetate, manganese chloride, and betaine is added, and the DNA is treated with a DNA or RNA ligase capable of intramolecular ligation of single-stranded DNA substrates to form the single-stranded circles.

The single-stranded circles may be used as a template for subsequent amplification and analysis. Thus, in certain embodiments, the single-stranded circles are subjected to rolling-circle amplification. Amplification reagents are added to initiate the RCA reaction, producing up to microgram quantities or more of whole-genome amplified DNA for downstream analysis.

In certain other embodiments, the single-stranded circles are subjected to inverse PCR. Inverse PCR on circular DNA would provide the ability to generate amplicons containing flanking sequence of a breakpoint in circumstances where only a single sequence is known. Because the DNA is fragmented and the break points are random and unknown, standard PCR will fail frequently because often the break point will lie within the desired amplicon sequence. Inverse PCR on circular DNA would be successful regardless of the location of the breakpoint, thereby providing an ability to recover these amplicons and allowing for more efficient analysis of fragmented DNA with random breakpoints.

In one aspect, the invention provides a method of analyzing a biological sample. Thus, single-stranded DNA circles are first generated according to certain embodiments of the invention, followed by amplification of the single-stranded DNA circles; and analyzing the amplified single-stranded DNA circles. The amplified nucleic acid may be analyzed using any conventional method, such as sequencing, genotyping, comparative genomic hybridization, etc. In certain embodiments, the amplified nucleic acid is analyzed by whole genome sequencing. In other embodiments, the amplified nucleic acid is analyzed by targeted sequencing of the amplified single-stranded DNA circles.

In certain embodiments, the amplified nucleic acid is analyzed by sequencing using a DNA sequencing method whose read length is longer than the initial fragment size, i.e., prior to circularization. Exemplary methods may include nanopore sequencing and the SMRT (Single Molecule Real Time) sequencing technology from Pacific Biosciences. The sequence information obtained through these methods is more accurate by virtue of redundant sequencing, to compensate for the quality of the methods used, which are error prone.

In another aspect, the invention provides a method of detecting chromosomal rearrangement breakpoints from a biological sample. Thus, single-stranded DNA circles are first generated according to certain embodiments of the invention, followed by amplification of the single-stranded DNA circles; sequencing the amplified single-stranded DNA circles; and identifying chromosomal rearrangement breakpoints by comparing the sequences to a known reference sequence.

In some embodiments, kits for analyzing a biological sample are provided. In one embodiment, the kit comprises an extractant for treating the biological sample to release nucleic acids; a reagent for neutralizing the extractant; and a ligase that is capable of template-independent, intramolecular ligation of a single-stranded DNA sequence. In some embodiments, the extractant comprises proteinase K or a detergent. In some embodiments, the reagent for neutralizing the extractant comprises a proteinase K inhibitor or a cyclodextrin. In other embodiments, the ligase is a TS2126 RNA ligase (CircLigase II).

In one embodiment, the kit further comprises a solid matrix for drying the sample mixture.

In one embodiment, the kit further comprises enzyme(s) that repair some types of DNA damage. An exemplary enzyme may be a polynucleotide kinase such as a T4 PNK.

The kit may further comprise buffers (e.g., HEPES), DNA amplification regents (e.g., DNA polymerase, primers, dNTPs) and other reagents (e.g., MnCl$_2$, betaine) that are employed for the generation of single-stranded DNA circle by the provided methods. In some embodiments, the kit may include Phi29 DNA polymerase and random/partially constrained primers. The kit may include other reagents for nucleic acid analysis, such as reagents for sequencing the amplified nucleic acid sample. The kits may further include instructions for the generation of single-stranded DNA circles from linear DNA.

EXAMPLES

Example 1

Circularization Reaction in the Presence of Neutralized Extractant

Neutralized tissue digestion buffer was prepared by combining a solution of 30 mM HEPES, pH 8.0, 1 mM EDTA, 0.5% SDS, 0.01% Tween-20, and 2 mg/ml proteinase K with 2.5% alpha cyclodextrin and 0.25 mM proteinase K inhibitor (EMD Millipore, peptide sequence MeOSuc-Ala-Ala-Pro-Phe-CH$_2$Cl (SEQ ID NO: 1)). Increasing amounts of this neutralized buffer were added to a 30 µl circularization reaction containing 48 mM HEPES, pH 8.0, 0.5 mM DTT, 49.3 mM KOAc, 2.5 mM MnCl$_2$, 500 mM betaine, and 0.5 µM phosphorylated 64-mer oligonucleotide. After incubation for 60 min at 60° C., reactions were analyzed by electrophoresis through a 10% polyacrylamide gel using TBE buffer, stained with SYBR Gold (Invitrogen) and visualized using a Typhoon imager (FIG. 2 (A)). Relative intensities of linear and circular species were quantified and plotted as percent of oligonucleotide circularized (FIG. 2 (B)).

As shown in FIG. 2, tissue digestion buffer is neutralized and tested for its effect on the circularization reaction. Even in the presence of 6 µl of tissue digest buffer, the efficiency of circularization of a 64-mer phosphorylated oligonucleotide is relatively unaffected in a 30 µl reaction, indicating that the tissue digestion buffer has been neutralized successfully.

Example 2: Amplification Reaction Using High Tm Primers is More Resistant to Carryover Inhibition A carryover mixture was prepared by drying 1 µl of lysis buffer onto a 1.2 mm FTA punch and performing neutralization. This carryover mixture contained 53 mM HEPES, pH 8.0, 0.18 mM EDTA, 0.05% SDS, 0.07 mg/ml proteinase K, 0.01% Tween-20, 0.8% alpha-cyclodextrin, 16.7 mM NaCl, 2.6 mM Tris, pH 7.9, 3.3 mM MgCl$_2$, 2.2 mM DTT, 25 µM ATP, 3.3 µM dNTPs, 2.5 mM MnCl$_2$, 500 mM betaine, 0.6 mM uric acid, and 0.08 mM proteinase K inhibitor. Increasing amounts of the carryover mixture were added to a 20 µl amplification reaction containing 20 mM KCl, 1 ng human genomic DNA, and the indicated random hexamer. Real-time amplification was performed by adding a small amount of SYBR green I to the amplification mixture and monitoring fluorescence increase over time in a Tecan plate reader. The time at which fluorescence reached a threshold of 4000 RFU was determined and plotted.

Figure 3:
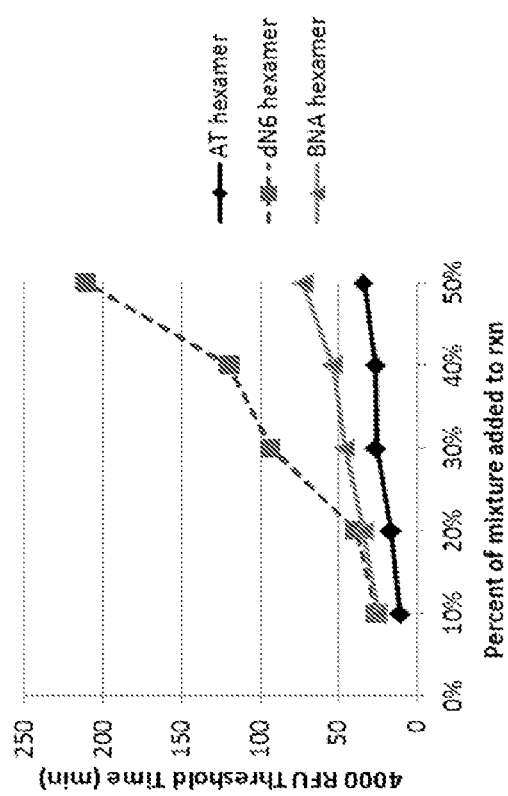

FIG. 3 shows that whole-genome amplification reactions using either locked nucleic acid (LNA) or bridged nucleic acid (BNA)-modified random hexamers are more resistant to the presence of carryover inhibitors than reactions performed using a standard dN6 hexamer. Whereas the carryover of buffer components from the circularization reactions had a significant negative impact on the whole-genome amplification reaction using standard dN6 hexamer "NNNN*N*N", the inhibitory effect could be reduced by utilizing the LNA or BNA hexamer. The AT random hexamer has the sequence "+N+N(atN)(atN)(atN)*N", where + precedes an LNA base, * represents a phosphorothioate linkage, and (atN) represents a random mixture of 2-amino-dA, t-thio-dT, normal dC, and normal dG. The BNA hexamer has the sequence "–N–NNN*N*N" where "–" represents a BNA3 base (Biosynthesis). The use of the LNA or BNA-containing random hexamer allows for the use of less pure input material and for the amplification reaction to be conducted with components from the single-tube lysis, neutralization, repair, and circularization reaction of DNA from a biological sample without prior DNA purification.

Example 3

Amplification of Fragmented DNA Directly From Human Tissue

A deparaffinized section containing fixed SKOV3 xenograft tissue was scraped and underwent digestion in a lysis buffer containing 30 mM HEPES, pH 8.0, 1 mM EDTA, 0.5% SDS, 0.01% Tween-20, and 0.5 mg/ml proteinase K for 1 hour at 50° C. 1 µl lysate corresponding to approximately 1 ng of fragmented DNA was applied to a 1.2 mm FTA punch and allowed to dry. After neutralization in 5 µl with 2.5% alpha cyclodextrin and 0.25 mM proteinase K inhibitor (EMD Millipore, peptide sequence MeOSuc-Ala-Ala-Pro-Phe-CH$_2$Cl (SEQ ID NO: 1)), tissue lysate was used directly for repair and circularization. Repair reactions (10 µl) additionally contained 50 mM NaCl, 10 mM MgCl$_2$, 5 mM DTT, 75 µM ATP, 10 mM dNTPs, NEB enzymes *E. coli* polymerase I (1 U), T4 DNA ligase (40 U), Endonuclease IV (1 U), UDG (0.5 U), APE1 (1 U), and T4 polynucleotide kinase (0.5 U) and were incubated at 37° C. for 30 min followed by 85° C. for 15 min. The repair reaction were heated at 95° C. to denature the DNA, then quickly cooled on ice. Circularization reactions (30 µl) additionally contained 48 mM HEPES, pH 8.0, 0.5 mM DTT, 49.3 mM KOAc, 2.5 mM MnCl$_2$, 500 mM betaine. 120 U of CircLigase II (EpiCentre) was added, then reactions were incubated at 60° C. for 8 hours, then enzyme was inactivated by incubating at 80° C. for 10 minutes. Rolling-circle amplification reactions (60 µl) additionally contained 25 mM HEPES, pH 8.0, 19 mM MgCl$_2$, 400 µM dNTPs, 1 mM TCEP, 2.5% PEG-8000, 40 µM AT random hexamer, and 1.2 µg Phi29 DNA polymerase. Real-time amplification was performed by adding a small amount of SYBR green I to the amplification mixture and monitoring fluorescence increase over time in a Tecan plate reader (FIG. 4 (A)). The time at which fluorescence reached a threshold of 4000 RFU was determined and plotted in (FIG. 4 (B)). Top graph in FIG. 4 (A) corresponds to first data point in FIG. 4 (B) (K562), and bottom graph in FIG. 4 (A) corresponds to last data point in FIG. 4 (B) (FFPE plus repair and circularization).

FIG. 4 shows an example of direct amplification of fragmented DNA from human tissue. SKOV3 xenograft tissue was digested, the reaction was neutralized, and lysate corresponding to approximately 1 ng of the fragmented DNA was subjected to combinations of repair and circularization as indicated. Whole-genome amplification kinetics of the treated DNA shows that reactions that underwent circularization proceeded more rapidly, indicating that the fragmented DNA had successfully undergone circularization under these conditions and the amplification reaction had switched to a faster rolling-circle mechanism.

Example 4

Improved Sequence Coverage and SNP Detection After Repair and Circularization

A piece of SKOV3 xenograft tissue was fixed in 25% neutral-buffered formalin for 10 days at room temperature and DNA was purified. 50 ng of this fragmented DNA was subjected to repair and/or circularization as described in FIG. 3 except that the repair enzyme mixture contained only T4 polynucleotide kinase, UDG, and 0.8 U Fpg. Real-time DNA amplification was performed by adding a small amount of SYBR green I to the amplification mixture and monitoring fluorescence increase over time in a Tecan plate reader (FIG. 5A). Following purification, amplified DNA was analyzed by preparing a barcoded Illumina TruSeq Amplicon Cancer Panel library and sequencing using the MiSeq sequencer (Illumina) according to manufacturer's instructions. Reads were mapped to the human genomic DNA reference sequence and depth of coverage was plotted (FIG. 5B). In addition, a variant analysis was performed to determine the number of SNPs detected and the coverage depths at these positions (FIG. 5B).

In FIG. 5, DNA from highly formalin-fixed SKOV3 xenograft tissue underwent a multi-step single-tube amplification protocol involving tissue lysis, neutralization, treatment with repair and/or circularization enzymes as indicated, followed by amplification of the DNA via RCA. The faster amplification kinetics of reactions in which the DNA had undergone circularization indicates successful neutralization of the proteinase K and SDS from the tissue lysis step and conversion of the fragmented DNA to a circular form. In addition, amplified DNA was analyzed by preparing an Illumina TruSeq Amplicon Cancer Panel library and sequencing using the MiSeq sequencer (Illumina). Results demonstrated significantly improved depth of coverage for reactions that underwent repair and circularization. Comparing the unamplified FFPE DNA sequence to reference genome sequence revealed a total of 21 single-nucleotide polymorphisms (SNPs). For the amplified DNA, we found that more of these SNPs were detected and the average coverage depth at these positions was higher when DNA was treated with repair and circularization.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A method for generating single-stranded DNA circles from a biological sample, the method comprising:
   A) treating the biological sample with an extractant to release nucleic acids, thereby forming a sample mixture, and subjecting the sample mixture to a drying step on a solid matrix, wherein the solid matrix comprises glass fiber filters or quartz fiber filters (QMA), and the solid matrix is impregnated with a chelating agent, an anionic surfactant, or a combination thereof;
   B) neutralizing the extractant, wherein the extractant is neutralized by adding a sequestrant comprising a proteinase K inhibitor;
   C) denaturing the released nucleic acids to generate single-stranded DNA;
   D) contacting the single-stranded DNA with a ligase that is capable of template-independent, intramolecular ligation of a single-stranded DNA sequence to generate the single-stranded DNA circles; and
   E) amplifying the single-stranded DNA circles via rolling circle amplification, wherein the single-stranded DNA circles are amplified with primers comprising one or more nucleotide analogues selected from a locked nucleic acid, a 2-Amino-dA, or a 2-Thio-dT,
   wherein the quantity of DNA extracted from the biological sample is limiting or of low quality, and wherein all the steps of the method are performed without any intermediate nucleic acid isolation or nucleic acid purification.

2. The method of claim 1, wherein the single-stranded DNA circles are amplified via rolling circle amplification followed by PCR or inverse PCR.

3. The method of claim 1, wherein the extractant further comprises a detergent.

4. The method of claim 1, wherein the ligase is a TS2126 RNA ligase.

5. The method of claim 1, wherein the biological sample is an FFPE tissue sample, fixed individual cells, blood plasma, ancient tissue sample, or an environmentally exposed sample.

6. The method of claim 1, wherein the biological sample is from a region of interest of an FFPE tissue section on a slide or individual cells of interest from fixed cells on a slide.

7. The method of claim 1, further comprising, between steps B) and C), a step of enzymatically repairing DNA damage.

\* \* \* \* \*

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<223> OTHER INFORMATION: N-term MeOSuc
<220> FEATURE:
<223> OTHER INFORMATION: C-term CH2Cl

<400> SEQUENCE: 1

Ala Ala Pro Phe
1
```